United States Patent
Metzger et al.

[11] 3,954,730
[45] May 4, 1976

[54] 6-(SUBSTITUTED-CYCLOALKYLCARBOXAMIDE) PENICILLANIC ACIDS

[75] Inventors: Karl Georg Metzger; Gunther Schmidt, both of Wuppertal, Germany

[73] Assignee: Bayer Aktiengesellschaft, Germany

[22] Filed: Oct. 21, 1974

[21] Appl. No.: 516,359

[30] Foreign Application Priority Data
Oct. 25, 1973  Germany............................ 2353584

[52] U.S. Cl............................... 260/239.1; 424/271
[51] Int. Cl.²............................................ C07D 499/74
[58] Field of Search................................. 260/239.1

[56] References Cited
UNITED STATES PATENTS

| | | |
|---|---|---|
| 3,041,333 | 6/1962 | Chow et al................ 260/239.1 |
| 3,174,964 | 3/1965 | Hobbs et al............... 260/239.1 |
| 3,245,983 | 4/1966 | Doyle et al. .............. 260/239.1 |
| 3,494,915 | 2/1970 | Alburn et al.............. 260/239.1 |
| 3,532,744 | 10/1970 | Fletcher et al............ 260/239.1 |
| 3,538,083 | 11/1970 | Grant et al............... 260/239.1 |
| 3,553,201 | 1/1971 | Clark et al............... 260/239.1 |
| 3,573,279 | 3/1971 | Alburn et al.............. 260/239.1 |

OTHER PUBLICATIONS
Chemical Abstr., Vol. 60, Col. 1759(H) at 1760(c) (1964).
Hobbs, et al., J. Med. & Pharm. Chem. Vol. 4, pp. 207–210 (1961).

Primary Examiner—Gerald A. Schwartz

[57] ABSTRACT

Penicillins of the formula

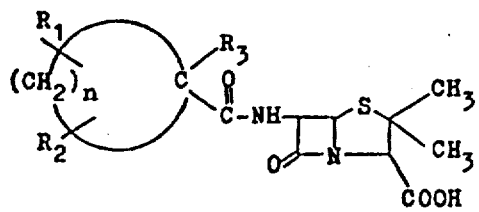

or a pharmaceutically-acceptable, nontoxic salt thereof,
wherein
$R_1$ and $R_2$ are the same or different and each is hydrogen, fluorine, chlorine or bromine; or when $R_2$ is hydrogen, $R_1$ can also be cyano, hydroxyl, azido, amino or nitro; or
$R_1$ and $R_2$ are bonded to a ring carbon atom and constitute a single oxygen atom;
$R_3$ is hydrogen, methyl, chlorine, bromine, cyano, methoxy or carboxyl; and
$n$ is 2 to 7;
are useful for their antibacterial activity.

16 Claims, No Drawings

6-(SUBSTITUTED-CYCLOALKYLCARBOXA-MIDE) PENICILLANIC ACIDS

The present invention relates to penicillins, to a process for their production, pharmaceutical compositions wherein said penicillins are the active ingredient, and to methods of treating bacterial infections in humans and animals which comprises administering said compounds to such humans or animals. In addition, the present invention includes growth-promoting compositions wherein said penicillins are the active ingredients and animal fodders, including methods of improving fodder utilization in animals utilizing said penicillins.

It is known in the art that certain 6-amino-penicillanic acid derivatives exhibit good antimicrobial activity. However, compounds in which halogen-substituted alicyclic carboxylic acids have been condensed with 6-aminopenicillanic acid (6-APA) have not been disclosed.

More particularly, the present invention is concerned with penicillins of the formula

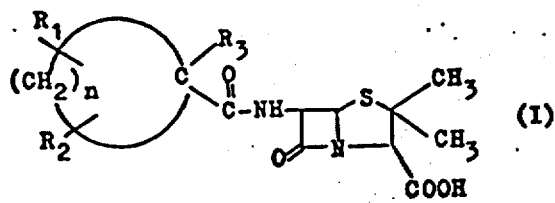

or a pharmaceutically-acceptable, nontoxic salt thereof,
wherein
$R_1$ and $R_2$ are the same or different and each is hydrogen, fluorine, chlorine or bromine; or when $R_2$ is hydrogen, $R_1$ can also be cyano, hydroxyl, azido, amino or nitro; or
$R_1$ and $R_2$ are bonded to a ring carbon atom and constitute a single oxygen atom;
$R_3$ is hydrogen, methyl, chlorine, bromine, cyano, methoxy or carboxyl; and
$n$ is 2 to 7.

These penicillins are produced by reacting 6-APA or a derivative thereof of the formula

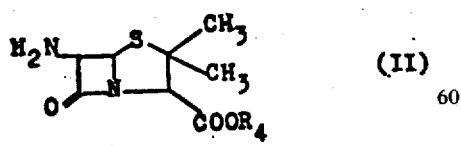

wherein
$R_4$ is hydrogen, triethylammonium, trialkylsilyl of 1 to 6 carbon atoms, or an alkali metal cation, with a compound of the formula

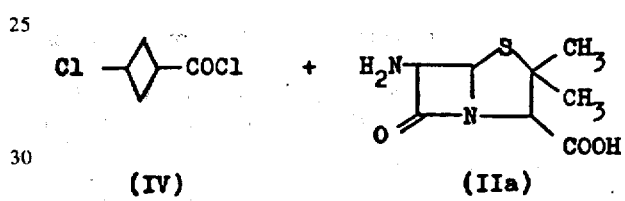

wherein $R_1$, $R_2$, $R_3$ and $n$ are as above defined, and X is hydroxyl or a reactive group which is split off in the acylation of the amino group.

The penicillins of the present invention are useful for their antibacterial activity, and, in particular, exhibit greater antibacterial activity against certain microorganisms than do commercially available products such as Penicillin G, Penicillin V or Azidocillin.

If, for example, 3-chloro-cyclobutane-carboxylic acid chloride (IV) and 6-APA (IIa) are used as starting materials, the course of the reaction can be represented by the following equation:

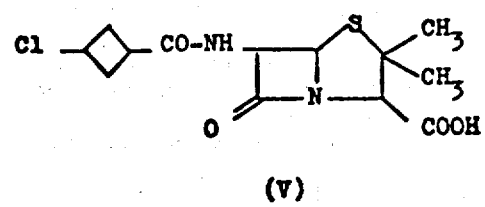

6-(3-chloro-cyclobutylcarboxamido)-penicillanic acid (V) is obtained as its sodium salt.

In the formulas I and II, the structural element

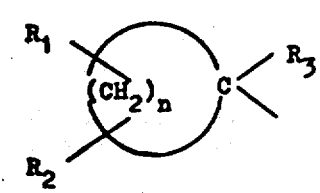

is one of the following radicals:

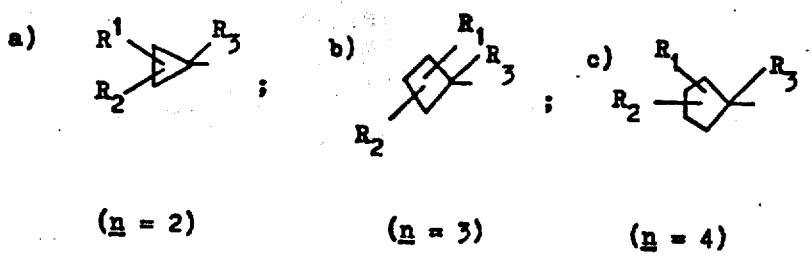

(n = 2)  (n = 3)  (n = 4)

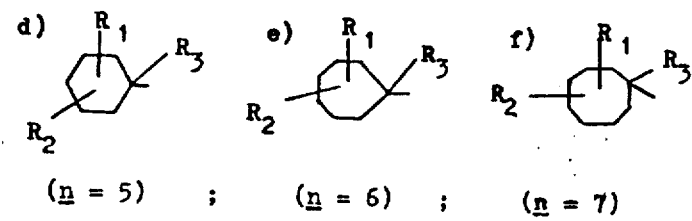

(n = 5) ;  (n = 6) ;  (n = 7)

According to one embodiment of the present invention $R_1$ is hydrogen, chlorine, or bromine; or, when $R_2$ is hydrogen, $R_1$ is hydrogen, chlorine, bromine or cyano; and $R_2$ is hydrogen, chlorine or bromine.

According to another embodiment of the present invention if neither $R_1$ nor $R_2$ are hydrogen, $R_1$ and $R_2$ are the same moiety.

According to another embodiment of the present invention $R_1$ and $R_2$, together with a ring carbon atom, form a carbonyl group; and $R_3$ is hydrogen, methyl, chlorine, bromine or cyano.

According to another embodiment of the present invention $R_1$ and $R_2$ are the same or different and each is hydrogen fluorine, chlorine, or bromine; or when $R_2$ is hydrogen, $R_1$ can also be cyano; or $R_1$ and $R_2$, together with a ring carbon atom, form a carbonyl group;

$R_3$ is hydrogen, methyl or chlorine; and n is 2, 3, 4, 5, or 6.

According to another embodiment of the present invention $R_1$ and $R_2$ are the same or different and each is hydrogen, chlorine, or bromine; or, when $R_2$ is hydrogen, $R_1$ can also be cyano; or $R_1$ and $R_2$ together with a ring carbon atom, form a carbonyl moiety;

$R_3$ is hydrogen, methyl, chlorine, bromine or cyano; and n is 2, 3, 4 or 5.

In the tralkylsilyl moiety $R_4$, the alkyl moieties may be either the same or different. Preferably, they are the same. Methyl, ethyl and n-propyl are preferred with methyl being particularly preferred. When $R_4$ is an alkali metal cation, sodium and potassium are particularly preferred.

According to another embodiment of the present invention, n is preferably to 2 to 5.

When X is a reactive group which is split off during the course of the acylation of the amino group, X can, for example, be azido; alkoxy, preferably of 1 to 6 and especially of 1 to 4 carbon atoms, unsubstituted or substituted by cyanomethoxy or a —O—COY moiety wherein Y is alkyl, especially of 1 to 4 carbon atoms; aryl, for example, phenyl; alkoxy, preferably of 1 to 4 carbon atoms and particularly methoxy or ethoxy. It is especially preferred that X is halogen, especially chlorine or bromine.

The salts of the penicillins of formula I include the salts formed at the acid carboxyl group with inorganic or organic bases and ammonia. Representative bases include: alkali metal and alkaline earth metal hydroxides, carbonates and bicarbonates, such as sodium, potassium, magnesium and calcium hydroxide, sodium, potassium and calcium carbonate, sodium and potassium bicarbonate and aluminum hydroxide. Representative salts formed with inorganic bases include sodium, potassium, magnesium, calcium, aluminum and ammonium salts. Salts formed with amines include di- and tri- alkylamines such as triethylamine, ethanolamine, procaine, dibenzylamine, N,N'-dibenzylethylenediamine, N-benzyl-β-phenylethylamine, N-methylmorpholine and N-ethylmorpholine, 1-ephenamine, dehydroabietylamine, N,N'-bis-dehydroabietylethylenediamine and N-alkylpiperidines.

The compounds of formula II which are used as starting materials according to the above process are known in the art. They may be obtained from Penicillin G by fermentative of chemical processes such as are described in German Auslegeschrift No. 1,111,778 and in Doyle, Nayler and Rolinson, British Patent No. 870,396 (1961) and in F. R. Batchelor et al., Nature (London), 183, 257 (1959).

The compounds of formula III which are used as starting materials in the above process are either known or can be prepared according to techniques per se known in the art (see *Organic Syntheses*, vol. 51, pages 73–75 (1971); A. J. Vogel, *J. Chem. Soc.*, 1929, 1,487–1,494; H. C. H. Carpenter and W. H. Perkin, *J. Chem. Soc.*, 75, 921–934 (1899); Belgian Patent No. 777,705).

Compounds of the formula III can thus be prepared, for example, in accordance with the following equation ($R_1$, $R_2$, $R_3$ and n having the above-mentioned meaning):

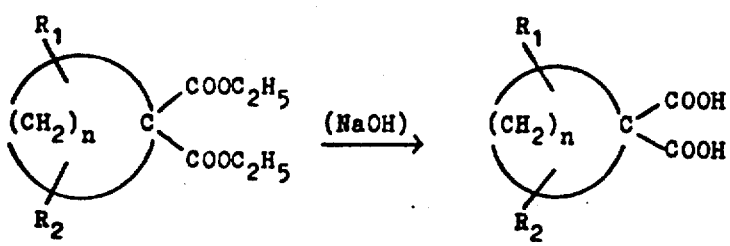

1. Halogenation, for example with $SO_2Cl_2$
2. Decarboxylation

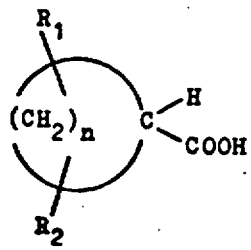

$\downarrow$ ($P\ Hal_5$ or $SOHal_2$, Hal = for example, Cl)

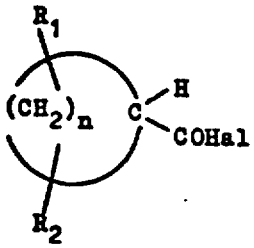

Further compounds of the formula III can be prepared, for example, in accordance with the following equation wherein Hal is halogen; for example, chlorine or bromine;
$R_5$ is methyl or ethyl; and
$R_6$ is hydrogen or methyl:

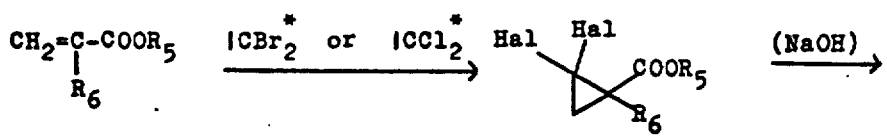

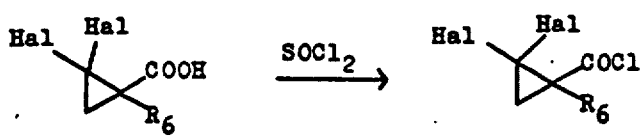

* = halocarbenes

Representative starting materials of formula III include:

2,2-dichloro-1-methyl-cyclopropane-carboxylic acid chloride,
2,2-dibromo-1-methyl-cyclopropane-carboxylic acid chloride,
2,2-difluoro-1-methyl-cyclopropane-carboxylic acid chloride,
2,2-dichloro-1-methyl-cyclopropane-carboxylic acid bromide,
2,2-dichloro-1-cyclopropanecarboxylic acid chloride,
2,2-dibromo-1-cyclopropanecarboxylic acid chloride,
2,2-difluoro-1-cyclopropanecarboxylic acid chloride,
2,2-difluoro-1-cyclopropanecarboxylic acid bromide,
2-cyano-1-cyclopropanecarboxylic acid chloride,
2-cyano-1-methyl-cyclopropanecarboxylic acid chloride,
3-chloro-1-cyclobutanecarboxylic acid chloride,
3-bromo-1-cyclobutanecarboxylic acid chloride,
3-fluoro-1-cyclobutanecarboxylic acid chloride,
cyclopropanecarboxylic acid chloride,
cyclobutanecarboxylic acid chloride,
cyclopentanecarboxylic acid chloride,
cyclohexanecarbocyclic acid chloride,
1-cyanocyclobutanecarboxylic acid chloride,
1-methylcyclobutanecarboxylic acid chloride,
1-chlorocyclobutanecarboxylic acid chloride,
1-chlorocyclobutanecarboxylic acid bromide, 4-chloro-1-cyclopentanecarboxylic acid chloride,
4-fluoro-1-cyclopentanecarboxylic acid chloride,
4-bromo-1-cyclopentanecarboxylic acid chloride,
3,4-dichloro-1-cyclopentanecarboxylic acid chloride,
3,4-dibromo-1-cyclopentanecarboxylic acid chloride,
3,4-difluoro-1-cyclopentanecarboxylic acid chloride,
cyclopentanone-2-carboxylic acid chloride,
cyclopentanone-2-chloro-carboxylic acid chloride,
4-chloro-1-cyclohexanecarboxylic acid chloride,
4-fluoro-1-cyclohexanecarboxylic acid chloride,
4-bromo-1-cyclohexanecarboxylic acid chloride,
4,5-dichloro-1-cyclohexanecarboxylic acid chloride,
4,5-dibromo-1-cyclohexanecarboxylic acid chloride,
4,5-difluoro-1-cyclohexanecarboxylic acid chloride,
4,5-dimethyl-1-cyclohexanecarboxylic acid chloride,
4-chloro-5-methyl-1-cyclohexanecarboxylic acid chloride,
1-bromo-1-cyclobutanecarboxylic acid chloride,
1-bromo-1-cyclopentanecarboxylic acid chloride,
1-chloro-1-cyclohexanecarboxylic acid chloride,
1-bromo-1-cyclohexanecarboxylic acid chloride,
2-bromo-1-cyclohexanecarboxylic acid chloride and
1-chloro-cycloheptanecarboxylic acid chloride.

The compounds of formula III can be used either as cis/trans isomer mixtures or in the pure stereoisomeric forms, i.e., the cis or the trans form.

The process of the present invention is generally carried out in the presence of a diluent which is generally an organic solvent. Especially suitable diluents include alkylketones (for example, acetone), ethers (for example, tetrahydrofuran (THF) and dioxane), alkylnitriles (for example, acetonitrile), dimethylformamide (DMF), dimethylsulphoxide, halogenated hydrocarbons (for example, methylene chloride), and mixtures of these solvents with one another and with water.

Except when X=OH and $R_4$ = H, the reaction in the process of the invention between the compounds II and III proceeds with the elimination of an acid or acid derivative, and it is therefore preferred to carry it out in the presence of an acid-binding agent. In principle any acid-binding agent can be used. Suitable agents include inorganic and organic bases, such as alkali metal or alkaline earth metal hydroxides, carbonates or bicarbonates (for example, sodium, potassium or calcium hydroxide, sodium, potassium or calcium carbonate or sodium or potassium carbonate), aliphatic amines (for example, triethylamine), and heterocyclic bases (for example, N-methyl-morpholine). The pH value of the reaction mixture can be maintained, by continuous or incremental addition of these bases, at any desired value, preferably at pH 6.5 to 9.2

The reaction temperatures can be varied within a substantial range. In general, the reaction is carried out at between −20°C and +50°C, and preferably between −15°C and + 20°C.

The reaction can be carried out under atmospheric pressure but also under elevated pressure. In general, atmospheric pressure is used.

When carrying out the process according to the present invention, the reactants are preferably reacted with one another in equimolecular amounts. However, it can be desirable to use one of the two reactants in excess in order to facilitate the isolation of the desired penicillin and/or to increase the yields.

For example, the reactants of the formula III can be employed in an excess of 10 to 30 per cent.

The new free penicillin of the formula I and their salts can be interconverted in any suitable manner; methods for such interconversion are known in the art.

The isolation and, if desired, purification of the compounds of the invention, are carried out in a known manner in accordance with generally customary methods of organic chemistry.

The following compounds are representative of those of the present invention:

6-(3-chloro-cyclobutylcarboxamido)-penicillanic acid,
6-(3-bromo-cyclobutylcarboxamido)-penicillanic acid,
6-(3-fluoro-cyclobutylcarboxamido)-penicillanic acid,
6-(2,2-dichloro-1-methyl-cyclopropylcarboxamido)-penicillanic acid,
6-(2,2-dibromo-1-methyl-cyclopropylcarboxamido)-penicillanic acid,
6-(2,2-difluoro-1-methyl-cyclopropylcarboxamido)-penicillanic acid,
6-(2-cyano-1-cyclopropylcarboxamido)-penicillanic acid,
6-(1-cyano-1-cyclobutylcarboxamido)-penicillanic acid,
6-(1-cyano-1-cyclopentylcarboxamido)-penicillanic acid,
6-(4-chloro-1-cyclopentylcarboxamido)-penicillanic acid,
6-(4-fluoro-1-cyclopentylcarboxamido)-penicillanic acid,
6-(4-bromo-1-cyclopentylcarboxamido)-penicillanic acid,
6-(3,4-dichloro-cyclopentylcarboxamido)-penicillanic acid,
6-(3,4-difluoro-cyclopentylcarboxamido)-penicillanic acid,
6-(3,4-dibromo-cyclopentylcarboxamido)-penicillanic acid,
6-(cyclopentanone-2-chloro-2-carboxamido)-penicillanic acid,
6-(cyclopentanone-2-methyl-2-carboxamido)-penicillanic acid,
6-(4-chloro-1-cyclohexylcarboxamido)-penicillanic acid,
6-(4-fluoro-1-cyclohexylcarboxamido)-penicillanic acid,
6(4-bromo-1-cyclohexylcarboxamido)-penicillanic acid,
6-(4,5-dichloro-1-cyclohexylcarboxamido)-penicillanic acid,
6-(4,5-difluoro-1-cyclohexylcarboxamido)-penicillanic acid,
6-(4,5-dibromo-1-cyclohexylcarboxamido)-penicillanic acid,
6-(1-chloro-1-cycloheptylcarboxamido)-penicillanic acid,
6-(2,2-dichloro-cyclopropylcarboxamido)-penicillanic acid,
6-(2-bromo-2-methyl-cyclopropylcarboxamido)-penicillanic acid,
6-(1-bromo-1-cyclobutylcarboxamido)-penicillanic acid,
6-(1-bromo-1-cyclopentylcarboxamido)-penicillanic acid,
6-(1-chloro-1-cyclohexylcarboxamido)-penicillanic acid,
6-(1-bromo-1-cyclohexylcarboxamido)-penicillanic acid and sodium and potassium salts of these penicillins.

The compounds of the present invention are characterized by strong antimicrobial activity and low toxicity. They are thus useful for the treatment of a broad range of Gram-positive and Gram-negative bacterial infections. They are also useful for preserving organic and inorganic materials such as polymers, lubricants, paints, fibers, leather, paper, timer, foodstuffs, water and the like.

Compounds of the present invention are particularly useful for the prophylaxis and treatment of topical and systemic infections caused by Gram-positive and Gram-negative microorganisms.

The following pathogens are representative of those against which the penicillins of the present invention are effective:

Micrococcaceae, such as Staphylococci (for example, *Staphylococcus aureus*, *Staph. epidermidis*, *Staph. aerogenes* and *Gaffkya tetragena* ("Staph". = Staphylococcus));

Lactobacteriaaceae, such as Streptococci (for example, *Streptococcus pyogenes*, α- or β-heamolytic Streptococci, non-(γ)-haemolytic Streptococci, *Str. viridans*, *Str. faecalis* (Enterococci), *Str. agalactiae*, *Str. lactis*, *Str. equi*, *Str. anaerobis* and *Diplococcus pneumoniae* (Pneumococci) ("Str." = Streptococcus));

Neisseriaceae, such as Neisseriae (for example, *Neisseria gonorrhoeae* (Gonococci), *N. meningitidis* (Meningococci), *N. catarrhalis* and *N. flava* ("N." = Neisseria);

Corynebacteriaceae, such as Corynebacteria (for example, *Corynebacterium diphtheriae*, *C. pyogenes*, *C. diphtheroides*, *C. acnes*, *C. parvum*, *C. bovis*, *C. renale*, *C. ovis* and *C. murisepticum*);

Enterobacteriaceae, such as *Escherichiae bacteria*, (for example, *Escherichia coli*), Enterobacter bacteria (for example, *E. aerogenes* and *E. cloacae*) ("E." = Enterobacter) Klebsiella bacteria (for example, *K. pneumoniae*) ("K." = Klebsiella), Erwiniae (for example, Erwinia spec.), Serratia (for example, *Serratia marcescens*, Proteae bacteria of the Proteus group: Proteus (for example, Pr. vulgaris and Pr. mirabilis) ("Pr." = Proteus)

Salmonelleae: Salmonella bacteria (for example, *Sammonella paratyphi A and B*, *S. typhi*, *S. enteritidis*, *S. cholerae suis* and *S. typhimurium* ("S." = Salmonella); and Shigella bacteria (for example, *Shigella dysenteriae*, *Sh. ambigua*, *Sh. flexneri*, *Sh. boydiii and Sh. sonnei* ("Sh". = Shigella));

Parvobacteriaceae or Brucellaceae, such as Pasteurella bacteria (for example, *Pasteurella multocida*, *Past, pestis* (Yersinia), *Past, pseudotuberculosis* and *Past. tularensis* ("Past". = Pasteurella)), Brucella bacteria (for example, *Brucella abortus*, *Br. melitensis* and *Br. suis* ("Br". = Brucella)), Haemophilus bacteria (for example, *Haemophilus influenzae*, *H. ducreyi H. suis*, *H. canis* and *H. aegypticus* ("H". = Haemophilus)), Bordetella bacteria (for example, *Bordetella pertussis* and *B. bronchiseptica* ("B." = Bordetella)) and Moraxella bacteria, (for example, *Moraxella lacunata*);

Bacteroidaceae, such as Bacteroides bacteria (for example, *Bacteroides fragilis* and *B. serpens* ("B". = Bacteroides)), Fusiforme bacteria (for example, *Fusobacterium fusiforme*) and Sphaerophorus bacteria (for example, *Sphaerophorus necrophorus*, *Sph. pyrogenes* ("Sph". = Sphaerophorus)); vaginocola);

Bacillaceae, such as aerobic spore-forming organisms, (for example, *Bacillus anthracis*, *B. subtilis* and *B. cereus* ("B". = Bacillus)) and anaerobic spore-forming organisms - Clostridia (for example, *Clostridium perfringens*, *Cl. septicium*, *Cl. oedematiens*, *Cl. histolyticum*, *Cl. tetani* and *Cl. botulinum* ("Cl". = Clostridium));

Illnesses of the respiratory passages, the pharyngeal cavity, otitis, pharyngitis, pneumonia, peritonitis, pyelonephritis, cystitis, endocarditis, systemic infections, bronchitis, and arthritis may all be treated with the penicillins of the present invention.

The following in vitro and in vivo data demonstrates the antimicrobial activity, particularly the antibacterial activity, of the penicillins of the present invention, as well as their effectiveness upon oral administration.

Table 1, which follows, specifies the minimum inhibitory concentrations (MIC) in vitro, in U/ml of nutrient medium of typical compounds of the invention. They were determined in a liquid medium in a test tube series dilution test, the readings being taken after 24 hours incubation at 37°C.

The numbers allotted to the compounds of the invention in Table 1 correspond to the numbers of the Preparative Examples in which the preparation of the particular compounds are described.

The MIC is indicated by the non-turbid test tube in the dilution series. A complete medium of the following composition was used as the growth medium:

| | |
|---|---|
| Lab Lemco (Oxoid) | 10 g |
| Peptone (Difco) | 10 g |
| NaCl | 3 g |
| D(+) dextrose (Merck) | 10 g |
| Buffer pH 7.4 | 1,000 ml |

Table 1

| Compound from Example No. | MIC in U/ml | | | |
|---|---|---|---|---|
| | E. coli | | Staph. aureus | Ent. |
| | 14 | C 165 | 1756 | 133 | ATCC 9790 |
| 1 | 128 | — | 32–64 | 0.2 | 16–32 |
| 2 | 128 | — | 128 | 0.2 | 32 |
| 3 | 128–256 | — | — | 2–4 | 64–128 |
| 4 | 32–64 | 128–256 | 32–64 | 2–4 | 8–16 |
| 5 | 32–64 | 128 | 128 | 0.2 | 8 |
| 6 | 32 | 128 | 32–64 | 0.1 | 8–16 |
| 7 | 32 | 128 | 32–64 | 0.1 | 8–16 |
| 8 | 128 | — | — | 2–4 | 128 |
| 9 | 64 | — | 64 | 0.1 | 8–16 |

"E." = Escherichia
"Staph." = Staphylococcus
"Ent." = Enterococcus

It can be seen from this table that the compounds of the present invention exhibit strong antibacterial effects. Their activity extends both to Gram-positive and to Gram-negative bacteria.

The compounds of the present invention are active against genera of bacteria other than those mentioned in Table 1. This shown by the following experiment which was carried out with the compound of Example 1.

The compound of Example 1 was diluted with Muller-Hinton nutrient broth, with addition of 0.1% of glucose, to a content of 100 µg/ml. The nutrient solution contained $1 \times 10^5$ to $2 \times 10^5$ bacterial cells per milliliter. The test tubes containing this mixture were each incubated for 24 hours and the degree of turbidity was then determined. Freedom from turbidity indicated that the compound had exerted an anti-bacterial action. Cultures of the following bacteria were free from turbidity at a dosage of 100 µg/ml ("sp." = species):

E. coli BE; Salmonella sp.; Shigella sp.; Proteus indolnegativ, sp.; Pasteurella pseudotuberculosis; Brucella sp.;

Haemophilus influenzae; Bordetella bronciseptica; Staphylococcus aureus 133; Neisseria catarrhalis sp.; Diplococcus pneumoniae sp.; Streptococcus pyogenes W.; Enterococcus sp.; Lactobacillus sp.. Corynebacterium diphteriae gravis; Corynebacterium pyrogenes M; Clostridium botulinium; Clostridium tetani;

Table 2, which follows, shows the action of one of the compounds of the present invention against a series of bacteria in animal experiments in white mice. The white, mice of strain $CF_1$ were infected intraperitoneally with the particular species of bacteria indicated.

Table 2

Animal experiment with white mice:
Determination of the $ED_{50}$ after 24 hours.

| Germ | Dose in units of the compound of Example 1 per kg: | |
|---|---|---|
| | subcutaneous | oral |
| E.coli C 165 | 1 × 200,000 | — |
| Staphylococcus aureus 133 | 1 × 5,000 | 10,000 |

Treatment: 1 administration 30 minutes after infection

The $ED_{50}$ is the dose at which 50% of the infected animals still survive after 24 hours.

The pharmaceutical compositions of the present invention contain a major or minor amount, e.g. 0.1% to 99.5%, preferably 0.5% to 95% of active ingredient as above defined in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the router of administration and the nature and gravity of the illness, generally the dosage will be from 6 to 900, preferably 20 to 300, mg/kg of body weight per day. In some instances, a sufficient therapeutic effect can be obtained at a lower dose; while in others, a larger dose will be required. Individual administrations are preferably from 2 to 300, especially 5 to 100, mg/kg of body weight.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improved the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base, as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as pepperming oil or saccharin, and the like, can also be added.

Where appropriate, dosage unit formulations for oral administration can be microencapsulated. The formulation can also be prepared to prolong or sustain the release as, for example, by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as, for example, myristyl palmitate, or mixtures thereof.

Topical administration can be effected utilizing solid dosage unit forms such as powders or liquid or semi-liquid dosage unit forms such as solutions, suspensions, ointments, pastes, creams and gels. The powders are formulated utilizing such carriers as talc, bentonite, silicic acid, polyamide powder and the like. Liquid and semi-liquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 300 mg. to 90 g, preferably 1 g to 20 g of active agent.

While the routes of administration include oral, parenteral (i.e., intramuscular, intraperitoneal and intravenous), rectal, and topical, particularly preferred is parenteral administration, especially intravenous.

The preferred pharmaceutical compostions are therefore those in a form suitable for parenteral administration such as injectable (i.e., sterile and isotonic) solutions and ampoules of such solutions.

The pharmaceutical compositions of the present invention are also useful against penicillinase-producing bacteria. Other penicillins may be included such as prostaphin, i.e., Oxacillin and Dicloxacillin.

The following nonlimitative examples more particularly describe the present invention:

The β-lactam content of the compounds prepared was determined iodometrically.

All the intermediate compounds and compounds of the present invention described here gave, in the IR spectrum the bands which agree with their expected structure.

The compounds produced were subjected to an analytical counter-currrent distribution through 29 steps, using petroleum ether/ethyl acetate/dimethylformamide/water as the distribution system.

The NMR spectra of the compounds of the present invention prepared were recorded in CD$_3$OD solution.

Gas chromatography was used as an analytical test of the purity of many of the intermediate compounds.

In calculating the elementary analyses, the water content of the 6-APA drivatives is taken into account.

In the text which follows the abbreviations denote:

| THF | = tetrahydrofuran | min. | = minutes |
| EA | = ethyl acetate | i.v. | = in vacuo |
| 6-APA | = 6-aminopenicillanic acid | | |

EXAMPLE 1

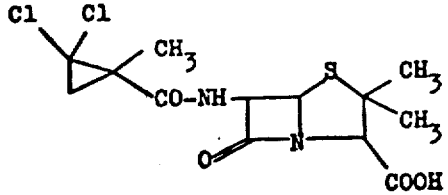

A. 7 g (0.0323 mol) of 6-aminopenicillanic acid (6-APA) are suspended in a mixture (120 ml) of THF and water (1:1). The suspension is adjusted to pH 7.8 to 8.0 by means of 2 N NaOH, while cooling with ice, and 6.95 g (0.0371 mol) of 2,2-dichloro-1-methyl-cyclopropanecarboxylic acid chloride dissolved in 35 ml of pure THF are added over the course of 25 minutes at +2°C to +5°C. The pH value of the reaction solution is kept at 7.2–7.5 up to the end of the experiment by further addition of 2 N sodium hydroxide solution. The reaction mixture is stirred for a further 20 minutes at +5° C and 20 minutes at +15°C. After distilling off the THF, the residual solution is diluted with 200 ml of water and extracted once with ethyl acetate (EA).

The aqueous phase, which has been separated off, is cooled to 0°C, covered with 200 ml of EA, with addition of 70 ml of methyl ethyl ketone, and acidified to a pH value of 2.0 with 2 N HCl.

The organic phase is separated off and the aqueous phase is extracted once more with 150 ml of EA.

The organic phases are combined, washed with water until neutral and dried over Na$_2$SO$_4$ for 20 minutes.

After distilling off the solvent, a light, rubbery product remains, which is taken up in 80 ml of absolute methanol and an equivalent amount of 1 molar sodium 2-ethylhexanoate in ether containing methanol.

The solution is gently concentrated to dryness i.v. and the residue is recrystallized from ether/n-pentane.

Yield (relative to 6-APA): 10.5 g (83.3%) of the sodium salt of 6-(2,2-dichloro-1-methyl-cyclopropylcarboxamido)-penicillanic acid (formula given above).

β-Lactam content: 74.5%

C$_{13}$H$_{15}$Cl$_2$N$_2$O$_4$ SNa (389.236) Calculated: C, 40.14; H, 3.89; Cl, 18.22; S, 8.4; N, 7.20%. Found: C, 39.6; H, 4.5; Cl, 18.1; S, 7.9; N, 6.1%.

NMR signals at δ (solvent CD$_3$OD): 1.4 (1H); 1.5–1.7 (9H); 2.1–2.2 (1H); 4.2 (1H); 5.5 ppm (2H).

B. 2,2-Dichloro-1-methyl-cyclopropanecarboxylic acid 4 g (0.0176 mol) of benzyltriethyl-ammonium chloride are added to 102 ml of 50% strength sodium hydroxide solution (1.27 mols). 50 g (0.5 mol) of methyl acrylate and 119.5 g (1.0 mol) of chloroform are added while stirring at a speed of 500–600 revolutions/minute and cooling to 5°–10°C. The reaction mixture is stirred for 24 hours at 20°–25°C, then diluted with cold water (500 ml) and extracted four times with 150 ml of petroleum ether and ether. The aqueous phase is acidified by means of concentrated HCl and extracted with chloroform/methyl ethyl ketone, and the extracts are dried over Ha$_2$SO$_4$.

The end product is isolated by vacuum distillation.

Boiling point (0.25 mm.Hg) : 76° C

Yield: 37.5 g (44.4%)

C$_5$H$_6$Cl$_2$O$_2$ (169.013) Calculated: C, 35.54; H, 3,58; Cl, 41.96%. Found: C, 34.9; H, 3.6; Cl, 42.0%.

NMR signals at δ (solvent CDCl$_3$): 1.4 (1H); 1.55–1.7 (3H); 2.3–2.4 (1H); 12.1 ppm (1H).

C. 2,2-Dichloro-1-methyl-cyclopropanecarboxylic acid chloride.

15 g (0.0887 mol) of 2,2-dichloro-1-methyl-cyclopropanecarboxylic acid are dissolved in 60 ml of methylene chloride and 50 ml of thionyl chloride are added.

The solution is kept under reflux for several hours. After distilling off the CH$_2$CL$_2$ and the excess SOCl$_2$, the residue is treated twice more with methylene chloride.

Yield: 15.4 g (92.8%)

C$_5$H$_5$Cl$_3$O (187.4)

Calculated: C, 32.03; H, 2.69; Cl, 56.72%.

Found: C, 31.7; H, 3.3; Cl, 56.2%.

The other starting compounds of this type are obtained analogously.

EXAMPLE 2

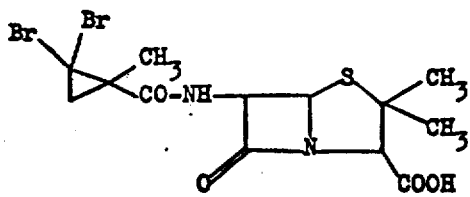

A. The sodium salt of the penicillin is prepared analogously to Example 1A from: 6 g (0.0278 mol) of 6-APA and 9.2 g (0.0332 mol) of 2,2-dibromo-1-methyl-cyclopropanecarboxylic acid chloride.

Yield: 11.2 g (84.2%) of the sodium salt of 6-(2,2-dibromo-1-methyl-cyclopropyl-carboxamido)-penicillanic acid $C_{13}H_{15}Br_2N_2O_4SNa$ (478.1) Calculated: C, 30,37; H, 3,73; H, 5.45; S, 6.24; Br, 31.09%. Found: C, 30.6; H, 3.7; N, 5.5; S, 7.0; Br, 32.6%.

β-Lactam content: 93.8%

NMR signals at (solvent CD$_3$OD): 1.25 (1H); 1.8–1.85 (9H); 2.2–2.4 (1H); 4.25 (1H); 5.5 ppm (2H).

B. 2,2-Dibromo-1-methyl-cyclopropanecarboxylic acid

The substituted cyclopropanecarboxylic acid is prepared analogously to Example 1B from 100 g (1mol) of methyl acrylate and 253 g (1 mol) of bromoform in the presence of 102 ml (1.27 mols) of 50% strength sodium hydroxide solution and 4 g (0.0176 mol) of benzyl-triethyl-ammonium chloride.

Yield: 79.6 g (30.9%)

Boiling point (0.2 mm.Hg) : 115°–120°C $C_5H_6Br_2O_2$ (257.9) Calculated: C, 23.29; H, 2.34; Br, 61.96%. Found: C, 23.4; H, 2.3; Br, 59.9%. C. 2,2-Dibromo-1-methyl-cyclopropanecarboxylic acid chloride The substituted cyclopropanecarboxylic acid chloride is prepared analogously to Example 1C from 35 g (0.136 mol) of 2,2-dibromo-1-methyl-cyclopropanecarboxylic acid and 110 ml of thionyl chloride in the presence of CH$_2$Cl$_2$.

Yield: 37.3 g (99.3%)

$C_5H_5Br_2$ ClO (276.4) Calculated: C, 21.73; H, 1.82; Br, 57.83; Cl, 12.83%. Found: C, 21.1; H, 1.8; Br, 57.0; Cl, 12.8%.

The other starting compounds of this type are obtainable analogously.

EXAMPLE 3

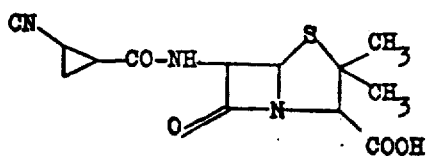

A. The sodium salt of this penicillin is prepared analogously to Example 1A from; 4.88 g (0.0226 mol) of 6-APA and 3.2 g (0.0248 mol) of 2-cyano-1-cyclopropanecarboxylic acid chloride.

Yield: 5.2 g (69.5%) of the sodium salt of 6-(2-cyano-1-cyclopropylcarboxamido)-penicillanic acid.

$C_{13}H_{14}N_3O_4SNa.1H_2O$ (331.3) Calculated: C, 44.69; H, 4.62; N, 12.03; S, 9.18%. Found: C, 44.3; H, 5.4; N, 10.9; S, 9.7%.

β-Lactam content: 60.9%

NMR signals at δ (solvent CD$_3$OD): 1.6–1.7 (6H); 1.9 (2H); 3.45 (1H); 3.75 (1H); 4.2 (1H); 5.5 ppm (2H).

B. 2-Cyano-1-cyclopropanecarboxylic acid 20 g. (0.144 mol) of 2-cyano-1-cyclopropanecarboxylic acid ethyl ester are dissolved in 60 ml of CH$_3$OH and saponified overnight at room temperature (approx. 20°C) with 44 ml of 4 N NaOH. The solvent is then stripped off in vacuo and 100 ml of water are added to the residue. The water phase is acidified with 2 HCl while cooling with ice and the product is isolated, by ethyl acetate extraction, as a white solid material.

Yield: 11.7 g (73.1%)

$C_5H_5NO_2$ (111.1) Calculated: C, 54.05; H, 4.54; N, 12.61%. Found: C, 53.0; H, 4.6; N, 11.6%.

C. 2-Cyano-1-cyclopropanecarboxylic acid chloride

The acid chloride is prepared analogously to Example 1C from 11.7 g (0.105 mol) of 2-cyano-1-cyclopropanecarboxylic acid and 80 ml of SOCl$_2$.

Yield: 9.8 g (72.0%)

$C_5H_4ClNO$ (129.5) Calculated: C, 46.37; H, 4.11; N, 10.81; Cl, 27.37%. Found: C, 47.9; H, 4.2; N, 10.6; Cl, 21.7%.

The remaining starting compounds of this type are obtainable analogously.

EXAMPLE 4

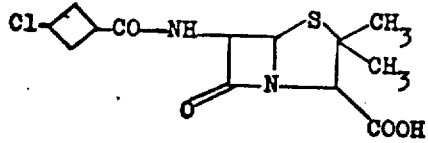

A. The sodium salt of this penicillin is prepared by a method based on Example 1A, from: 6.5 g (0.0301 mol) of 6-APA and 5.05 g (0.033 mol) of 3-chloro-1-cyclobutanecarboxylic acid chloride.

The sodium salt is recrystallized from a small amount of chloroform and a large amount of diisopropyl ether.

Yield: 7.1g (72.3%) of the sodium salt of 6-(3-chloro-cyclobutylcarboxamido)-penicillanic acid.

$C_{13}H_{16}ClN_2O_4Na.2H_2O$ (358.8) Calculated: C, 43.52; H, 5.62; N, 7.80; S, 8.94; Cl, 9.88%. Found: C, 43.50; H, 6.8; N, 6.2; S, 7.9; Cl, 9.6%.

β-Lactam content: 67.5%

NMR signals at δ (solvent CD$_3$OD): 1.58–1.67 (6H); 2.5–2.8 (4H): 3.2–3.4 (1H); 4.2 (1H); 4.4–4.6 (1H); 5.5 ppm (2H).

B. 3-Chloro-1-cyclobutanecarboxylic acid 50 g (0.347 mol) of cyclobutane-1,1-dicarboxylic acid and 435 ml of benzene are initially introduced into a 2 liter three-necked flask equipped with a reflux condenser, stirrer and CaCl$_2$ tube and heated under reflux for approx. 2 hours. Thereafter, about 60 ml of the benzene/water mixture are distilled off. 29.5 ml (0.364 mol) of sulphuryl chloride are then added to the reaction solution from a dropping funnel over the course of 40 minutes. Stirring and heating are continued. While sulphuryl chloride drips in, 1.16 g (0.004 mol) of benzoyl peroxide are added in small portions through the condenser.

After the dropwise addition of SO$_2$Cl$_2$ and the addition of benzoyl peroxide, the reaction mixture is kept for 22 hours under reflux.

After boiling under reflux for 22 hours, benzene is distilled off and the residue which remains is heated to 190°–210° C for 45 minutes in order to achieve complete decarboxylation. The black residue is then distilled immediately through a 6 cm long Vigreux column.

1. First fraction: 6.4 g (13.7%)
2. Main fraction: 20.5 g (44.1%)
Boiling point (10 mm.Hg) 125°–130°C.
$C_5H_7ClO_2$ (134.6) Calculated: C, 44.62; H, 5.25; Cl, 26.34%. Found: C, 45.4; H, 5.4; Cl, 26.4%.

NMR signals of the main fraction (No. 2) at δ (solvent $CCl_4$): 2.5–2.8 (4H); 3.1–3.3 (1H); 4.4–4.7 (1H); 12.1 ppm (1H).

C. 3-Chloro-1-cyclobutanecarboxylic acid chloride

The acid chloride is prepared analogously to Example 1C from 3 g (0.0223 mol) of 3-chloro-1-cyclobutanecarboxylic acid and 20 ml of thionyl chloride in the presence of 20 ml of $CH_2Cl_2$.

Yield: 1.6 g (46.8%)
$C_5H_6Cl_2O$ (153.0) Calculated: C, 39.25; H, 3.29; Cl, 46.34%. Found: C, 41.4; H, 4.5; Cl, 46.1%.

NMR signals at δ (solvent $CCl_4$): 2.6–3.0 (4H); 3.1–3.4 (1H); 4.2–4.5 ppm (1H). obtainable analogously.

EXAMPLE 5

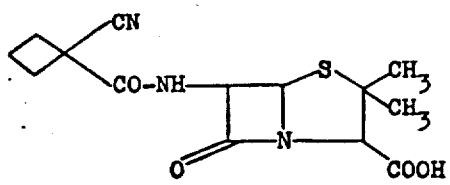

A. The sodium salt of this penicillin is prepared analogously to Example 1A form: 7.00 g (0.0323 mol) of 6-APA and 5.32 g (0.0379 mol) of 1-cyano-1-cyclobutanecarboxylic acid chloride.

Yield: 7.5 g (67.0%) of the sodium salt of 6(1-cyano-1-cyclobutylcarboxamido)-penicillanic acid $C_{14}H_{16}N_3O_4SNa \cdot 1H_2O$ (363.4) Calculated: C, 46.28; H, 4.99; N, 11.56; S, 8.82%. Found: C, 46.5; H, 4.9; N, 11.2; S, 7.6%.

β-Lactam content: 71.8%
NMR signals at δ (solvent $CD_3OD$): 1.6–1.68 (6H); 2.14–2.35 (2H); 2.59–2.7 (4H); 4.22 (1H); 5.38–5.6 ppm (2H).

B. 1-Cyano-1-cyclobutanecarboxylic acid ethyl ester 25 g (1.09 mol) of sodium are dissolved in 350 ml of pure $C_2H_5OH$ and the solution is cooled to +5°C. 125 g (1.11 mols) of cyanoacetic acid ethyl ester are then added, followed shortly thereafter by 141.3 g (0.7 mol) of 1,3-dibromopropane.

After boiling water reflux for about 3 hours, the ethanol is distilled off, the residue which remains is treated with $H_2O$ and the aqueous solution is extracted with ether. The combined ether phases are washed with water and twice with 10% strength $K_2CO_3$ solution and dried over $CaCl_2$. After distilling off the ether, a colorless oil is obtained, which is distilled in steam. All steam distillates are now saturated with $(NH_4)_2SO_4$ and extracted with ether.

After drying the ether extracts over $CaCl_2$, the solvent is evaporated off; this leaves a light oil, which is fractionally distilled twice.

Boiling point 208°
Yield: 35 g (32.7%)
$C_8H_{11}NO_2$ (153.2) Calculated: C, 62.72; H, 7.24; N, 9.14%. Found: C, 59.3; H, 7.0; N, 9.3%.

C. 1-Cyano-1-cyclobutanecarboxylic acid 20 g (0.131 mol) of 1-cyano-1-cyclobutanecarboxylic acid ethyl ester are dissolved in 60 ml of methanol and saponified with 40 ml of 4 N NaOH for about 12 hours at 23°C.

A white, resinous residue is isolated, which after trituration in dry petroleum ether can easily be filtered off and dried.

Yield: 11.0 g (67.5%)
During drying in a high vacuum at 80°–100°C, the $CN-CH_2-COOH$ formed as a by-product is sublimed off. $C_6H_7NO_2$ (125.1) Calculated: C, 57.60; N, 5.64; N, 11.20%. Found: C, 55.4; N, 5.6; N, 11.1%.

NMR signals at δ (solvent $CDCl_3$): 2.15–2.55 (2H); 2.7–2.9 4H); 10.3 ppm (1H).

D. 1-Cyano-1-cyclobutanecarboxylic acid chloride

The acid chloride is prepared analogously to Example 1C from 9.5 g (0.076 mol) of 1-cyano-1-cyclobutanecarboxylic acid and 60 ml of $SOCl_2$.

Yield: 8.3 g (76.1%)
$C_6H_6ClNO$ (143.6) Calculated: C, 50.19; H, 4.21; Cl, 24.69%. Found: C, 39.7; H, 4.4; Cl, 24.8%.

The other starting compounds of this type are obtainable analogously.

EXAMPLE 6

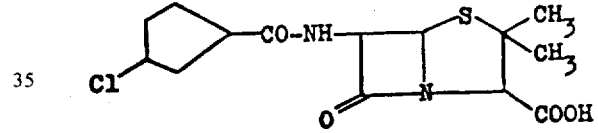

A. The sodium salt of this penicillin is prepared analogously to Example 1A from: 5.0 g (0.0232 mol) of 6-APA and 4.65 g (0.0278 mol) of 4-chloro-1-cyclopentanecarboxylic acid chloride.

After recrystallization from THF/diisopropyl ether, 7.1 g (58.6%) of the sodium salt of 6-(4-chloro-1-cyclopentylcarboxamide)-penicillanic acid are obtained.

$C_{14}H_{18}ClN_2O_4SNa \cdot 1H_2O$ (386.8) Calculated: C, 43.47; H, 5.21; N, 7.24; S, 8.29; Cl, 9.16%. Found: C, 44.5; H, 5.4; N, 6.7; S, 7.8; Cl, 10.5%.

β-Lactam content: 75.3%
NMR signals at δ (solvent: $CD_3OD$): 1.6–1.7 (6H); 2.05–2.35 (4H); 2.55–2.75 (2H); 3.3–3.4 (1H); 3.5–3.7 (1H); 4.2 (1H); 5.45–5.6 ppm (2H).

B. 4-Chloro-1-cyclopentanecarboxylic acid and 3,4-dichloro-1-cyclopentanecarboxylic acid These chlorine-substituted cyclopentanecarboxylic acids are prepared analogously to Example 4B from 46.0 g (0.291 mol) of cyclopentane-1,1-dicarboxylic acid dissolved in 450 ml of benzene, 49.5 ml (0.611 mol) of $SO_2Cl_2$ and 2.46 g (0.0101 mol) of benzoyl peroxide.

The chlorinated products are isolated as described in the preceding Example 4B; after decarboxylation, the residue is distilled in a high vacuum through a 10 cm long Vigreux column. 4 fractions are obtained:

1st fraction: boiling point (0.4 mm.Hg): 92°–94°C
2nd fraction: boiling point (0.3 mm.Hg): 94°–98°C
3rd fraction: boiling point (0.3 mm.Hg): 98°–102°C
4th fraction: boiling point (0.3 mm.Hg): 102°C

19

In detail, the fractions represent the following: 1st and 2nd fraction = 4-chloro-1-cyclopentanecarboxylic acid Yield: 12.9 g (30%)

$C_6H_9ClO_2$ (148.6) Calculated: C, 48.50; H, 6.11; Cl, 23.85%. Found: C, 46.8; H, 4.7; Cl, 24.3%. NMR signals at δ ($CDCl_3$): 2.1–2.3 (4H); 2.7–2.9 (2H); 3.5–3.7 (1H); 4.35–4.8 (1H); 11.65 ppm (1H).

3rd fraction; contains some 3,4-dichloro-1-cyclopentanecarboxylic acid; substance was discarded.

4sh fraction: = 3,4-dichloro-1-cyclopentanecarboxylic acid

Yield: 4.5 g (8.5%) $C_6H_8Cl_2O_2$ (183.0)

Calculated: C, 39.38; H, 4.41; Cl, 38.75%.

Found: C, 39.9; H, 4.0; Cl, 37.8%.

NMR signals at δ (solvent $CDCl_3$): 2.2–3.1 (4H); 3.2–3.4 (1H); 4.35–4.5 (2H); 11.2 ppm (1H).

C. 4-Chloro-1-cyclopentanecarboxylic acid chloride

The acid chloride is prepared analogously to Example 1C from 12.9 g (0.0868 mol) of 4-chloro-1-cyclopentanecarboxylic acid and 85 ml of thionyl chloride in the presence of $CH_2Cl_2$.

Yield: 12.9 g (89.0%)

$C_6H_8Cl_2O$ (167.0) Calculated: C, 43.15; H, 4.83; Cl, 42.46%. Found: C, 40.1; H, 3.7; Cl, 42.2%.

The other starting compounds of this type are obtainable analogously.

EXAMPLE 7

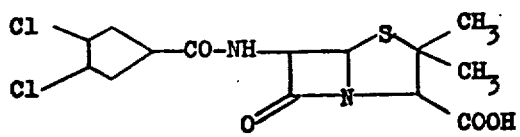

A. The sodium unit salt of this penicillin is prepared analogously to Example 1A from: 4.32 g (0.02 mol) of 6-APA and 4.8g. (0.0239 mol) of 3,4-dichloro-1-cyclopentanecarboxylic acid chloride. After recrystallization from THF/ether, 6.4 g (80.6%) of the sodium salt of 6-(3,4-dichlorocyclopentylcarboxamido)-penicillanic acid are obtained.

$C_{14}H_{17}Cl_2N_2O_4SNa.H_2O$ (421.3) Calculated: C, 39.91; H, 4.55; H, 6.65; S, 7.61; Cl, 16.83%. Found: C, 39.9; H, 4.9; N, 5.9; S, 7.1; Cl, 17.5%.

β-Lactam content: 74.7%

NMR signals at δ (solvent $CD_3OD$): 1.25–1.6 (6H); 2.2–3.1 (5H); 3.55 (1H); 4.35–4.55 (2H); 5.0–5.1 ppm (2H).

B. 3,4-Dichloro-1-cyclopentanecarboxylic acid chloride

The acid chloride is prepared analogously to Example 1C from 4.5 g (0,0246 mol) of 3,4-dichloro-1-cyclopentanecarboxylic acid (see Example 6B) and 80 ml of thionyl chloride in the presence of $CH_2Cl_2$.

Yield: 4.8 g (97.0%)

Gas chromatogram: single substance (Column: 2 m long, 2 mm φ; carrier material Chromosorb W; 100–120 mesh; liquid phase; silicone oil; isothermal oven: 150°C).

The other starting compounds of this type are obtained analogously.

EXAMPLE 8

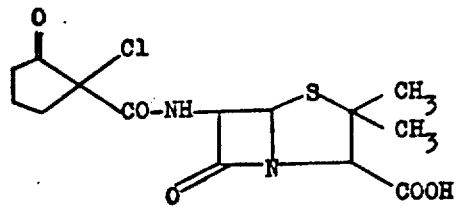

A. The sodium salt of this penicillin is prepared analogously to Example 1A from: 8 g (0.037 mol) of 6-APA and 8.05 g (0.0443 mol) of cyclopentanone-2-chloro-2-carboxylic acid chloride.

Yield: 8.9 g (63.0%)

Sodium salt of 6-(cyclopentanone-2-chloro-2-carboxamido)-penicillanic acid.

$C_{14}H_{17}ClN_2O_5SNa.1H_2O$ (382.8) Calculated: C, 41.95; H, 4.52; N, 6.99; S, 8.02; Cl, 8.84%.

Found: C, 42.0; H, 5.2; N, 6.4; S, 7.6; Cl, 8.8%.

β-Lactamm content: 73.9%

NMR signals at δ ($CD_3OD$): 1.6–1.68 (6H); 2.05–2.55 (6H); 4.25 (1H); 5.5–5.62 ppm (2H).

B. Cyclopentanone-2-chloro-2-carboxylic acid chloride

The acid chloride is prepared analogously to Example 1C from 9 g (0.0554 mol) of cyclopentanone-2-chloro-2-carboxylic acid and 80 ml of $SOCl_2$.

Yield: 9.8 g (98%)

$C_6H_6Cl_2O_2$ (181.0) Calculated: C, 39.82 H, 3.34; Cl, 39.17%. Found: C, 41.2; H, 3.8; Cl, 36.7%.

The other starting materials of this type are obtainable analogously.

EXAMPLE 9

Cl—⟨⟩—CO-NH—[β-lactam]—CH₃/CH₃/COOH

A. The sodium salt of this penicillin is prepared analogously to Example 1A from: 4.9 g (0.0227 mol) of 6-APA and 5.0 g (0.0272 mol) of 4-chloro-1-cyclohexanecarboxylic acid chloride.

Yield: 4.7 g (54.2%) of the sodium salt of 6-(4-chloro-1-cyclohexylcarboxamido)-penciillanic acid $C_{15}H_{20}ClN_2O_4SNa.H_2O$ (400.9)

Calculated: C, 44.95; H, 5.53; N, 6.99; S, 8.02; Cl, 8.84 %.

Found: C, 45.6; H, 6.4; N, 6.4; S, 8.0; C, 8.7 %.

β-Lactam content: 75.6%

NMR signals at δ (solvent $CD_3OD$): 1.58–2.4 (16H); 4.2 (1H); 5.48–5.63 ppm (2H).

B. 4-Chloro-1-cyclohexanecarboxylic acid and 4,5-dichloro-1-cyclohexanecarboxylic acid These chlorine-substituted cyclohexanecarboxylic acids are prepared analogously to Example 4B from 50 g (0.29 mol) of cyclohexane-1,1-dicarboxylic acid dissolved in 450 ml of benzene, 49.5 ml (0.66 mol) of $SO_2Cl_2$ and 2.46 g (0.0101 mol) of benzoyl peroxide.

The chlorinated products are isolated as described in the preceding Example 4B; after decarboxylation, the residue is fractionally distilled in a high vacuum:

1st fraction: boiling point (0.3 mm.Hg) = 90° (discarded)
2nd fraction: boiling point (0.2 mm.Hg) = 90°–99°
3rd fraction: boiling point (0.2 mm.Hg) = 99°–108°
4th fraction: boiling point (0.1 mm.Hg) > 108°

In detail, the fractions represent the following:
2nd fraction: 4-chloro-1-cyclohexanecarboxylic acid
Yield: 10.5 g
$C_7H_{11}ClO_2$ (162.6)
Calculated; C, 51.71; H, 6.82; Cl, 21.80%.
Found : C, 54.1; H, 6.1; Cl, 18.6%.

4th fraction: 4.5-dichloro-1-cyclohexane-carboxylic acid
Yield: 15.5 g
$C_7H_{10}Cl_2O_2$ (197.1)
Calculated: C, 42.68; H, 5.12; Cl 35.99%.
Found : C, 42.9; H, 4.9; Cl 34.7%.

C. 4-Chloro-1-cyclohexanecarboxylic acid chloride

The acid chloride is prepared analogously to Example 1C from 9.7 g (0.0595 mol) of 4-chloro-1-cyclohexanecarboxylic acid dissolved in 50 ml of $CH_2Cl_2$ and 60 ml of $SOCl_2$.
Yield: 10.6g (98.1%)
$C_7H_{10}Cl_2O$ (181.1)
Calculated: C, 46.45; H, 5.57; Cl, 39.17 %.
Found: C,48.1; H, 4.8; Cl, 37.1 %.

The other starting compounds of this type are obtainable analogously.

EXAMPLE 10

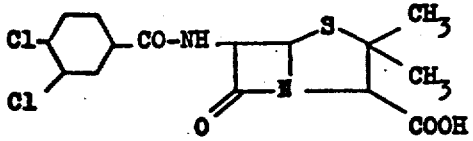

A. The sodium salt of this penicillin is prepared analogously to Example 1A from 6 g (0.0277 mol) of 6-APA and 6.9 g (0.032 mol) of 4,5-dichloro-1-cyclohexanecarboxylic acid chloride
Yield: 7.7 g (66.5%) of the sodium salt of 6-(4,5-dichloro-1-cyclohexylcarboxamido)-penicillanic acid.
$C_{15}H_{19}Cl_2N_2O_4SNa.1H_2O$ (435.3)
Calculated: C, 41.39; H, 4.86; N, 6.44; S, 7.37; Cl 16.29 %.
Found: C, 41.7 ; H, 5.2 ; N, 6.3 ; S, 7.2 ; Cl 16.6 %.
β-Lactam content: 77.4%
NMR signals at δ (solvent $CD_3OD$): 1.55–1.67 (6H): 1.9–2.6 (7H); 3.25–3.35 (1H); 3.7 (1H); 4.2 (1H); 5.4–5.5 ppm (2H).

B. 4,5-Dichloro-1-cyclohexanecarboxylic acid chloride

The acid chloride is prepared by a method based on Example 1C from 14.6 g (0.074 mol) of 4.5-dichloro-1-cyclohexanecarboxylic acid and 60 ml $SOCl_2$ in 50 ml of $CH_2Cl_2$.
Yield: 15.6 g (98.0%).
$C_7H_9Cl_3O$ (215.5)
Calculated: C, 39.02; H, 4.21; Cl, 49.35 %.
Found: C, 37.6; H, 4.2; Cl, 49.2 %.

The other starting compounds of this type are obtainable analogously.

EXAMPLE 11

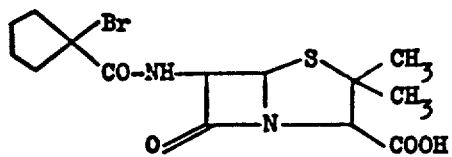

A. The sodium salt of this penicillin is prepared analogously to Example 1 from: 6 g (0.0277 mol) of 6-APA and 7.04 g (0.0333 mol) of 1-bromo-1-cyclopentanecarboxylic acid chloride.
Yield: 6.7 g (58.5%) of the sodium salt of 6-(1-bromo-1-cyclopentylcarboxamido)-penicillanic acid.
$C_{14}H_{18}BrN_2O_4SNa$ (413.3).
Calculated: C, 40.69; H, 4.39; N, 6.78; S, 7.77; Br,19.33 %.
Found: C, 40.6; H, 4.6; N, 5.8; S, 8.0; Br, 17.4 %.
β-Lactam content: 81.8%
NMR signals at δ (solvent $CD_3OD$): 1.6–1.7 (6H); 1.9–2.05 (4H); 2.3–2.4 (4H); 4.25 (1H); 5.4–5.65 ppm (2H).

B. 1-Bromo-1-cyclopentanecarboxylic acid 20 g (0.176 mol) of cyclopentaencarboxylic acid are mixed with red phosphorus (2.5 g). 17.9 ml (0.352 mol) of bromine are added dropwise thereto over the course of 2 hours; thereupon, a vigorous reaction is observed, with liberation of hydrogen bromide. The reaction contents are then stirred for 3 hours at 60°C. The oil, which shows a heavy dark coloration, is cooled and poured into water and the resulting reaction mixture is extracted three times with ether. The collected ether phases are washed with water and dried. After distilling off the ether, the oily residue is distilled in a high vacuum.

1. First fraction, boiling point (2 mm.Hg): 90°C
Yield: 9.0 g (26.6%)
2. Main fraction, boiling point (2 mm.Hg): 102°–104°C
Yield: 10.2 g (30.2%)
$C_6H_9BrO_2$ (193.0).
Calculated: C, 37.34; H 4.70 % .
Found: C, 40.1; H 5.2 %.
NMR signals at δ (solvent $CDCl_3$): 1.7–2.0 (4H); 2.2–2.3 (4H); 14.2 ppm (1H).

C. 1-Bromo-1-cyclopentanecarboxylic acid chloride

The acid chloride is prepared analogously to Example 1C from 10 g (0.0518 mol) of 1-bromo-1-cyclopentanecarboxylic acid dissolved in 30 ml of $CH_2Cl_2$ and 50 ml of $SOCl_2$.
Yield: 10.0 g (91.7%)
$C_6H_8BrClO$ (211.5).
Calculated: C, 34.07; H, 3.81; Cl, 16.76%.
Found: C, 36.4; H, 4.2; Cl, 15.7 %.
NMR signals at δ (solvent $CCl_4$): 1.85–2.2 (4H); 2.35–2.45 ppm (4H).

EXAMPLE 12

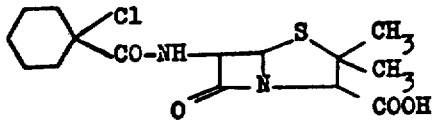

A. The sodium salt of this penicillin is prepared analogously to Example 1A from: 6 g (0.0277 mol) of 6-APA and 6.02 g (0.0332 mol) of 1-chloro-cyclohexanecarboxylic acid chloride.

Yield: 7.4 g (68.5%) of the sodium salt of 6-(1-chloro-1-cyclohexylcarboxamido)-penicillanic acid.

$C_{15}H_{20}ClN_2O_4SNa.1H_2O$ (400.9).

Calculated: C, 44.94; H, 5.53; N, 6.99; S, 8.02; Cl, 8.84 %.

Found: C, 45.6; H, 5.9; N, 6.8; S, 8.3; Cl, 6.7 %.

β-Lactam content: 74.1%

NMR signals at δ (solvent $CD_3OD$): 1.55–1.68 (6H); 1.7–2.1 (10H). 4.2 (1H); 5.45–5.0 ppm (2H).

B. 1-Chloro-1-cyclohexanecarboxylic acid chloride 80 g (0.547 mol) of cyclohexanecarboxylic acid chloride, 30 ml of carbon tetrachloride, 63 ml (0.778 mol) of $SO_2Cl_2$ and 1.5 g of benzoyl peroxide are heated for 10 hours. The chlorinated acid chloride is then distilled from the reaction mixture.

Boiling point (14 mm.Hg): 95°–110°C

Yield: 20.1 g (20.1%)

$C_7H_{10}Cl_2O$ (181.1).

Calculated: C, 46.44; H, 5.57 %.

Found: C, 46.8; H, 4.3 %.

NMR signals at 67 (solvent $CCl_4$): 1.45–2.3 ppm (10H).

EXAMPLE 13

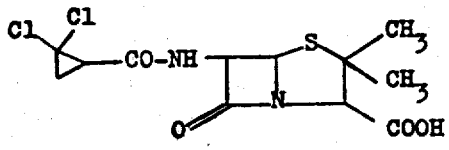

A. The sodium salt of this penicillin was prepared anlaogously to Example 1A from:

5 g (0.0231 mol) 6-APA and 4.6 g (0.0265 mol) 2,2-Dichloro-cyclopropane carboxylic acid chloride.

Yield: 6.2 g (71.5%) of the sodium salt of 6-(2,2-dichloro-cyclopropylcarboxamido)-penicillanic acid.

$C_{12}H_{13}Cl_2N_2O_4SNa.2H_2O$ (375.2).

Calculated: C, 35.05; H, 4.17; N, 6.82; S, 7.80; Cl, 17.24 %.

Found: C, 35.4; H, 5.0; N, 6.2; S, 7.9; CL, 19.0 %.

β-Lactam content: 87.2%

NMR-Signals at δ (solvent $CD_3OD$):

1.7–1.88 (6H); 1.98–2.32 (2H); 2.75–2.95 (1H); 4.32 (1H); 5.65 ppm (2H).

B. 1,1-Dichloro-2-vinylcyclopropane

Following the directions of R. C. Woodworth and P. S. Skell, [J.Amer.Chem.Soc. 79 2542–2544 (1957)], 240 g (4.4 mol) of 1,3-butadiene are reacted with chloroform in the presence of potassium tert.-butylate at −10°C. The reaction mixture is stirred overnight and thereafter treated with 1liter n-pentane and water and stirred. The organic phase is separated, washed with cold water, and dried over $Na_2SO_4$. After separation of the drying medium and evaporation of the solvent the residue is distilled. Yield 59 g of Bp. 120°–121°C.

C. 2,2-Dichloro-cyclopropane-1-carboxylic acid

Following a direction by M. Orchin and E. C. Herrick, [J.Org.Chem., 1959, (24), 139–140], 12.7 g (0.0926 mol) of 2,2-dichloro-cyclopropane carboxylic acid in 130 ml acetone are oxidized by means of 51 g $KMnO_4$ in 3 hours with the addition of 2.61 g $NaHCO_3$ at 0°C. Finally the reaction mixture is stirred overnight at room temperature. Acetone is evaporated off i.v., the residue treated with 150 ml of 40% $NaHSO_3$ solution, and the solution treated with enough 50% sulphuric acid with ice-cooling to produce a clear solution. The solution is extracted four times with ether, the extracts washed with 10% $NaHCO_3$-solution. The $NaHCO_3$-phase is now carefully acidified with half-concentrated HCl and again extracted with ether. The combined ethereal extracts are dried directly over $Na_2SO_4$, then $Na_2SO_4$ is separated off, the solvent evaporated i.v., and the residue distilled in high vacuum.

Yield 7.5 g (52.5%)

B.p.0.4 mm.Hg : 74°C $C_4H_4Cl_2O_2$ (154.9).

Calculated: C 31.00; H, 2.60; Cl, 45.75 % .

Found: C, 30.6; H, 2.5; Cl, 45.5 % .

NMR-Signals at δ (solvent $CCl_4$):

1.72–2.2 (2H); 2–2.7 (1H); 12.18 ppm (1H).

D. 2,2-Dichlorocyclopropanecarboxylic acid chloride.

As described in Example 1C the acid chloride is prepared from 12 g (0.0776 mol) 2,2-dichloro-Cyclopropanecarboxylic acid and 40 ml $SOCl_2$ in 50 ml $CH_2Cl_2$.

Yield: 8 g (59.8%)

B.p. (12 mm.Hg) : 58°C $C_4H_3Cl_3O$ (173.4).

Calculated: C, 27.71; H, 1.75; Cl, 61.34 % .

Founnd: C, 28.1; H, 2.3; Cl, 61.0 %.

NMR -Signals at δ (solvent $CCl_4$):

1.94–2.4 (2H); 3.0–3.28 ppm (1H).

EXAMPLE 14

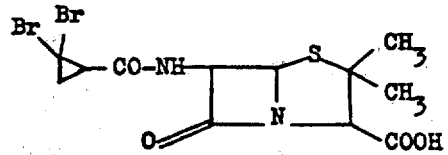

A. The sodium salt of this penicillin is prepared analogously to Example 1A from:

5 g (0.0231 mol) 6-APA and 7 g (0.0267 mol) 2,2-dibromo-cyclopropanecarboxylic acid chloride.

Yield: 6.2 g (58%) of the sodium salt of 6-(2,2-dibromo-cyclopropylcarboxamido)-penicillanic acid $C_{12}H_{13}Br_2N_2O_4SNa.1H_2O$ (464.1).

Calculated: C, 29.89; H, 3.14; N, 5.81; S, 6.65; BR, 33.16.

Found: C, 30.4; H, 3.9; N, 4.9; S, 6.7; Br, 32.3.

β-Lactam content: 87.4%

NMR-Signals at δ (solvent $CD_3OD$):

1.7–1.82 (6H); 2.08–2.38 (2H; 2.79–2.95 (1H); 4.3 (1H); 5.61 ppm (2H).

B. 1,1-Dibromo-2-vinylcyclopropane

Analogously to Example 13B,240 g (4.4 mol) 1,3-butadiene are reacted with 358.5 g (1.42 mol) of bromoform in the presence of potassium tert.-butylate (1.6 mol). The cyclopropane compound is distilled over a 20 cm.-long Vigreux column.

Yield: 130 g (40.6%)

B.p.(14 mm.Hg) : 55°C $C_5H_6Br_2$ (225.9)

Calculated: C, 26.58; H, 2.68; Br, 70.75 %.

Found: C, 2.63; H, 2.6; Br, 70.2 %.

NMR signals at δ (solvent $CCl_4$):

1.44–2.4 (3H); 5.12–5.8 ppm (3H).

C. 2,2-Dibromo-cyclopropane-1-carboxylic acid

Analogously to Example 13C the oxidation of the vinyl-cyclopropane derivative (67.8 g; 0.3 mol) is carried out in 425 ml acetone by means of 8.46 g NaHCO₃ and 166 g KMnO₄.

Yield 38.7 g (52.8%)

The crude product is triturated in n-pentane and thus brought to crystallization.

Melting point: 94°–95°C.

C₄H₄Br₂O₂ (243.9).

Calculated: C, 19.70 H, 1.65; Br 65.53 %.

Found: C, 20.4; H, 1.6; Br 64.4 %.

NMR-signals at δ (solvent CCl₄ ):

1.9–2.35 (2H); 2.52–2.8 (1H); 11.2 ppm (1H).

D. 2,2-Dibromocyclopropanecarboxylic acid chloride

As described in Example 1C, the acid chloride is prepared from 10 g (0.0411 mol) 2,2-dibromo-cyclopropanecarboxylic acid and 50 ml SOCl₂ in 30 ml CH₂Cl₂.

Yield: 7.6 g (70.4%)

B.p.(1 mm.Hg) : 48–50°C

C₄H₃ClBr₂O (262.3)

Calculated: C, 18.32; H, 1.15; Br, 60.93; Cl, 13.51 %.

Found: C, 16.7; H, 1.2; Br, 60.9; Cl, 13.6 %.

NMR-signals at δ (solvent CCl₄):

2.0–2.45 (2H); 3.0–3.28 ppm (1H).

EXAMPLE 15

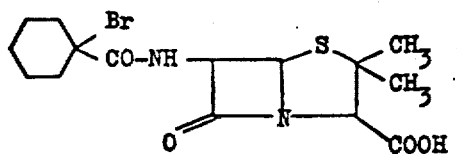

A. The sodium salt of this penicillin is prepared analogously to Example 1A from:

6g (0.0278 mol) 6-APA and 6.9 g (0.0306 mol) 1-bromo-1-cyclohexanecarboxylic acid chloride.

Yield: 9.1 g (76.5%) of the sodium salt of 6-(1-bromo-1-cyclohexylcarboxamido)-penicillanic acid C₁₅H₂₀BrN₂O₄SNa (427.3).

Calculated: C, 42.16; H, 4.72; N, 6.56; S, 7.51; Br 18.70 %.

Found: C, 42.9; H, 5.5; N, 6.1; S, 6.9; Br 16.8 %.

β-Lactam content: 68.4%

NMR-signals β (CD₃od):

1.1–1.2 (6H); 1.54–1.62 (6H); 2.1 (4H); 4.2 (1H); 5.4–5.6 ppm (2H).

B. 1-Bromo-1-cyclohexanecarboxylic acid

This compound is prepared analogously to Example 11B from:

35 g (0.275 mol) cyclohexanecarboxylic acid and 28.4 ml (0.548 mol) bromine with the addition of 3 g red phosphorus.

From the reaction mixture the main run is distilled at 100°C/2 mm. Hg.

Yield: 19.6 g (34.6%)

C₇H₁₁BrO₂ (207.1)

Calculated: C, 40.60; H, 5.36; Br, 38.58%.

Found: C, 45.3; H, 6.1; Br, 37.1 %.

NMR signals at δ (solvent CCl₄):

1.32–1.75 (6H); 2.08–2.18 (4H); 12.45 ppm (1H).

C. 1-Bromo-1-cyclohexanecarboxylic acid chloride

Analgously to Example 1C, the acid chloride is prepared from 17.8 g (0.086 mol) 1-bromo-1-cyclohexane-carboxylic acid dissolved in CH₂Cl₂ and 60 ml. SOCl₂.

Yield: 18.7 g (96.7%)

C₇H₁₀ClBrO (225.5).

Calculated: C, 37.28; H, 4.47; Cl, 15.72; Br 35.44 %.

Found: C, 39.7; H, 4.9; Cl, 15.8; Br 33.2 %.

What is claimed is:

1. A compound of the formula

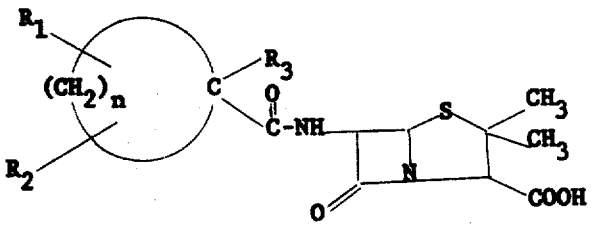

or a pharmaceutically-acceptable, nontoxic salt thereof, wherein one $R_1$ and $R_2$ is fluoro, chloro, bromo, cyano, hydroxyl, azido, amino or nitro and the other is hydrogen; $R_1$ and $R_2$ are both fluoro, chloro or bromo; or $R_1$ and $R_2$ taken together are oxo;

$R_3$ is hydrogen or methyl and $n$ is 2 to 7.

2. A compound according to claim 1 wherein $R_1$ is hydrogen, chloro or bromo and $R_2$ is chloro or bromo.

3. A compound according to claim 1 wherein $R_1$ and $R_2$ together are oxo.

4. A compound according to claim 1 wherein $R_3$ is hydrogen.

5. A compound according to claim 1 wherein $n$ is 2, 3, 4 or 5.

6. The sodium or potassium salt of a compound of claim 1.

7. The compound according to claim 1 which is

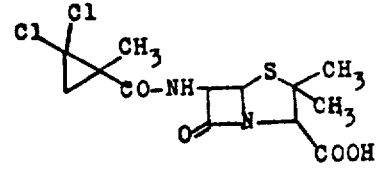

or the sodium salt thereof.

8. The compound according to claim 1 which is

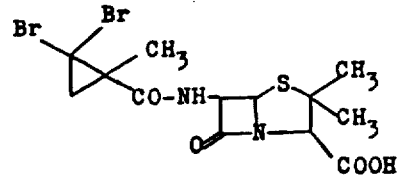

or the sodium salt thereof.

9. The compound according to claim 1 which is

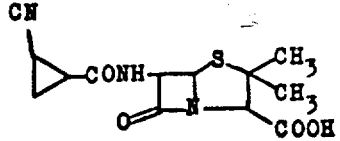

or the sodium salt thereof.
10. The compound according to claim 1 which is

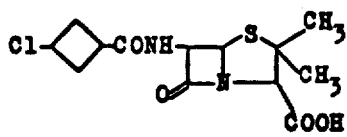

or the sodium salt thereof.
11. The compound according to claim 1 which is

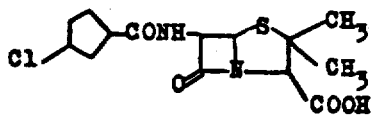

or the sodium salt salt thereof.
12. The compound according to claim 1 which is

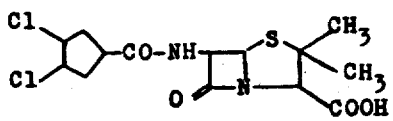

or the sodium salt thereof.
13. The compound according to claim 1 which is

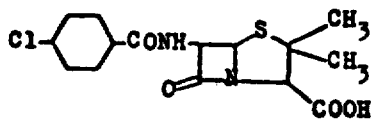

or the sodium salt thereof.
14. The compound according to claim 1 which is

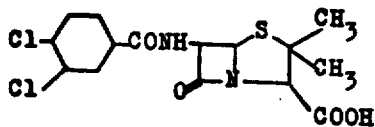

or the sodium salt thereof.
15. The compound according to claim 1 which is

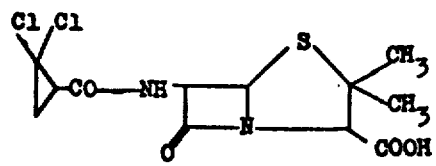

or the sodium salt thereof.
16. The compound according to claim 1 which is

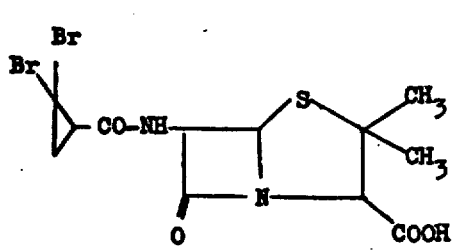

or the sodium salt thereof.

* * * * *